(12) United States Patent
Van Hecke et al.

(10) Patent No.: US 11,484,842 B2
(45) Date of Patent: Nov. 1, 2022

(54) METHOD AND APPARATUS FOR IN SITU PRODUCT RECOVERY

(71) Applicant: VITO NV, Mol (BE)

(72) Inventors: Wouter Van Hecke, Mol (BE); Helmut Elslander, Mol (BE); Karolien Vanbroekhoven, Mol (BE); Helene De Wever, Mol (BE); Herman Beckers, Mol (BE)

(73) Assignee: VITO NV, Mol (BE)

( * ) Notice: Subject to any disclaimer, the term of this patent is extended or adjusted under 35 U.S.C. 154(b) by 185 days.

(21) Appl. No.: 16/642,829

(22) PCT Filed: Sep. 4, 2018

(86) PCT No.: PCT/EP2018/073782
§ 371 (c)(1),
(2) Date: Feb. 27, 2020

(87) PCT Pub. No.: WO2019/048438
PCT Pub. Date: Mar. 14, 2019

(65) Prior Publication Data
US 2020/0197871 A1    Jun. 25, 2020

(30) Foreign Application Priority Data

Sep. 5, 2017 (EP) ..................................... 17189513
Sep. 5, 2017 (EP) ..................................... 17189514

(51) Int. Cl.
*B01D 63/16*    (2006.01)
*B01D 61/02*    (2006.01)
(Continued)

(52) U.S. Cl.
CPC ........... *B01D 63/16* (2013.01); *B01D 61/027* (2013.01); *B01D 61/145* (2013.01);
(Continued)

(58) Field of Classification Search
CPC .... B01D 63/16; B01D 61/027; B01D 61/145; B01D 61/147; B01D 61/362;
(Continued)

(56) References Cited

U.S. PATENT DOCUMENTS

| | | |
|---|---|---|
| 1,315,585 A | 9/1919 | Weizmann |
| 2,386,374 A | 10/1945 | Weizmann |
| 2013/0295661 A1* | 11/2013 | Roesch ................. C12P 7/6418 435/297.1 |

FOREIGN PATENT DOCUMENTS

| | | |
|---|---|---|
| BE | WO2012083390 A2 * | 6/2012 |
| DE | 102011080611 A1 | 2/2013 |
| WO | 2014088427 A1 | 6/2014 |

OTHER PUBLICATIONS

English language machine translation of DE102011080611, No Date, 10 pages.*
(Continued)

*Primary Examiner* — Pranav N Patel
(74) *Attorney, Agent, or Firm* — Kolitch Romano LLP

(57) ABSTRACT

A method of obtaining a compound may include adding a substrate to a medium in a reactor, and reacting the substrate in the reactor to form the compound. A first stream is separated from the reaction liquid through a first membrane. A second stream is separated from the reaction liquid through a second membrane. The first membrane is a filtration membrane and the second membrane is configured for liquid-gas or liquid-liquid extraction The first membrane and the second membrane are at least partially immersed in the medium and are moved relative to the reactor during the separation steps.

19 Claims, 6 Drawing Sheets

(51) Int. Cl.
  *B01D 61/14* (2006.01)
  *B01D 61/36* (2006.01)
  *C12M 1/00* (2006.01)
(52) U.S. Cl.
  CPC ......... *B01D 61/147* (2013.01); *B01D 61/362* (2013.01); *C12M 29/04* (2013.01); *C12M 47/10* (2013.01); *B01D 2311/2688* (2013.01); *B01D 2315/02* (2013.01); *B01D 2315/04* (2013.01); *B01D 2319/06* (2013.01); *B01D 2325/10* (2013.01)
(58) Field of Classification Search
  CPC ........ B01D 2311/2688; B01D 2315/02; B01D 2315/04; B01D 2319/06; B01D 2325/10; B01D 61/38; B01D 2311/04; B01D 61/58; B01D 61/14; B01D 2311/263; B01D 2317/08; C12M 29/04; C12M 47/10; C12M 21/04; C12M 29/20; Y02E 50/10; C12P 7/16; C12P 7/28; C12P 7/62; C12P 7/64; C12P 13/02; C12P 7/06
  See application file for complete search history.

(56) References Cited

OTHER PUBLICATIONS

Carstensen et al, Journal of Membrane Science 394-395 (2012) 1-36. (Year: 2012).*

Jiang et al, Chemical Engineering and Processing 62 (2012) 39-46. (Year: 2012).*

Lipnizki et al, Chem. Eng. Technol. 23 (2000) 7, pp. 569-577. (Year: 2000).*

Zuo et al, Korean J. Chem. Eng., 27(3), 881-885 (2010). (Year: 2010).*

Ylitervo et al, Environmental Technology, 2013, vol. 34, Nos. 13-14, 1711-1723. (Year: 2013).*

Qureshi, N et al: "Acetone butanol ethanol (ABE) recovery by pervaporation using silicalite-silicone composite membrane from fed-batch reacter of clostridium acetobutylicum", Journal of Membrane Science, Elsevier BV, NL, vol. 187, No. 1-2, Jun. 15, 2001.

Van Hecke, Wouter et al: "Biobutanol production from C5/C6 carbohydrates integrated with pervaporation: experimental results and conceptual plant design", Journal of Industrial Microbiology and Biotechnology, Basingstoke, GB, vol. 41, No. 1, Dec. 14, 2015.

Van Hecke, Wouter et al: "Investigation of lactate productivity in membrane bioreactors on C5/C6 carbohydrates", Journal of Membrane Science, Elsevier BV, NL, vol. 528, Jan. 25, 2017.

European Patent Office, International Search Report and Written Opinion of the International Search Authority of the International Searching Authority, dated Nov. 5, 2018, in PCT/EP2018/073782, which is the international application to this U.S. application.

* cited by examiner

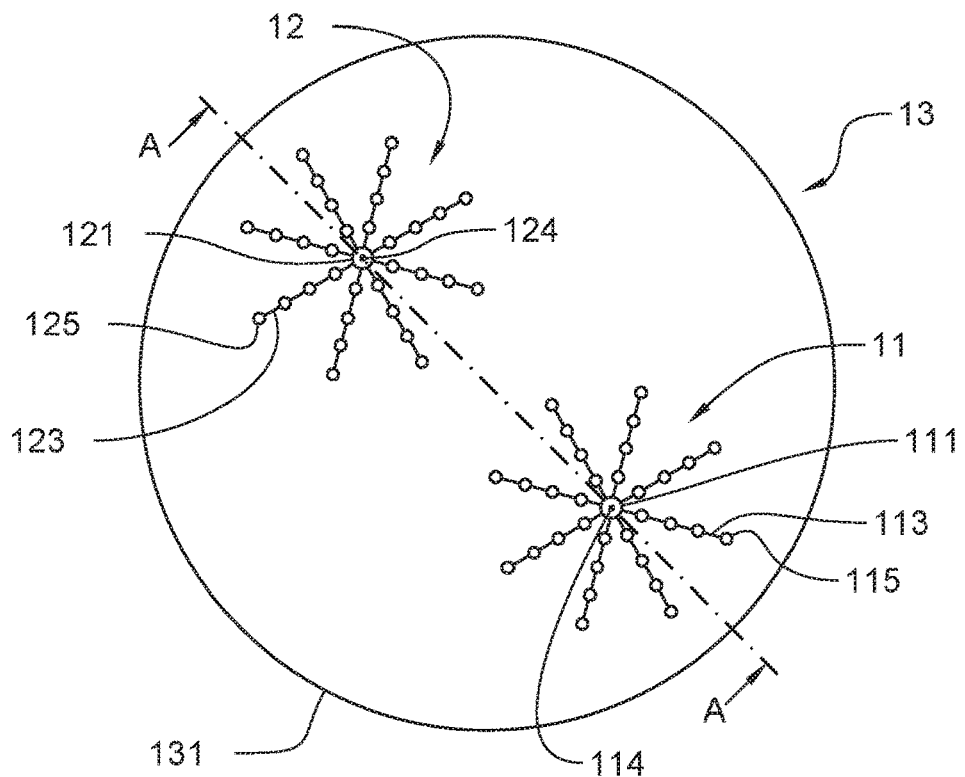
FIG 2A
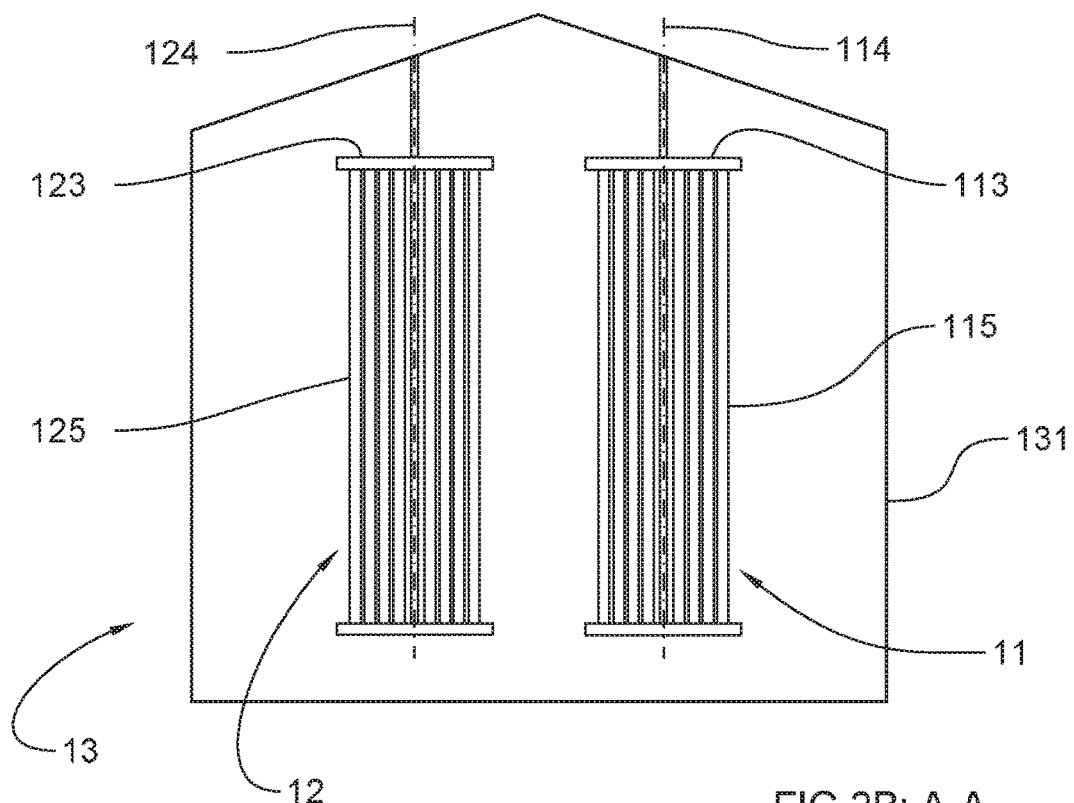
FIG 2B: A-A

METHOD AND APPARATUS FOR IN SITU PRODUCT RECOVERY

TECHNICAL FIELD

The present disclosure is related to methods and apparatuses for obtaining compounds, in particular organic compounds such as esters or amides, or organic solvents such as butanol or acetone. In particular, the present disclosure is related to methods and apparatuses for separating reaction products including the compound (continuously) from the reactor medium.

INTRODUCTION

The production of esters or amides often involves producing water or an alcohol such as methanol as a by-product. Since these reactions are equilibrium reactions, removing the by-products will shift the equilibrium to the right hand side, increasing product yield. Various options exist for withdrawing the by-products water and/or alcohol, such as using desiccants (e.g., molecular sieves), using a stripping gas, or by pervaporation. The use of desiccants is problematic during attempts of process upscaling, since they tend to pulverize, or cause problems in the downstream processes. The stripping gas in most cases entrains a large part of any volatile compounds present in the reactor.

The use of pervaporation for removing water and/or alcohol appears promising, but requires a profound control of process conditions. In a pervaporation unit, temperature and concentration gradients must be minimized, otherwise leading to losses in flux. To avoid these problems, a high degree of cross-flow is applied in order to minimize these gradients. This however requires a high energy input.

Early in the 20th century, the microorganism *Clostridium acetobutylicum* was found to convert carbohydrate containing feedstocks into acetone, ethanol and n-butanol, as described in U.S. Pat. Nos. 1,315,585, and 2,386,374. The method has been referred to since as the acetone n-butanol ethanol (ABE) fermentation process.

As generally known, and for example described in WO2013/086458 and WO2015/002913, n-butanol is an important industrial chemical, useful for example as a solvent, as a feedstock chemical in the plastics industry, as a fuel additive, as an ingredient in formulated products such as cosmetics, and as a food grade extractant in the food and flavor industry. Moreover, as a fuel, n-butanol has several advantages over ethanol. For instance, while n-butanol can be made from the same feedstocks as ethanol, it is, unlike ethanol, compatible with gasoline and diesel at higher ratios. Furthermore, n-butanol can also be used alone as a pure fuel in existing cars without modifications, it has been proposed as a building block to make jet fuel, etc.

A major drawback of n-butanol, however, is its toxicity to the producing culture in the ABE fermentation process, leading to cell inhibition. This is for example discussed in WO2013/086458 and EP 2283141. Because of such end product toxicity, solvent productivity is limited and the final concentration of product on a volume basis is low as well. Consequently, energy-intensive distillation operations are used, negatively affecting the economics of recovery of the different products. The high purification cost was one of the major reasons why the ABE fermentation was to a large extent abandoned during the 1950s and 1960s and replaced by petroleum based chemical plants for production of n-butanol and acetone. As such, each year 10 to 12 billion pounds of n-butanol are produced by petrochemical means. However, the depletion of today's fossil fuel stocks, the fluctuations in fossil fuel price and security of energy sources are the driving forces behind the current revival in n-biobutanol production. Accordingly, there is a high demand for efficient and sustainable methods for the production of n-butanol.

As nowadays there is an interest in development of technologies that use renewable resources for fuel production, the ABE fermentation is attracting renewed interest. However, solutions have to be found to avoid or reduce the n-butanol toxicity leading to cell inhibition and the associated low productivities and high purification costs.

In the art, it has already been proposed to alleviate the product inhibition by complementing the fermentation process with in situ product recovery (ISPR) technologies, such as adsorption, pervaporation, gas stripping, or liquid/liquid extraction. In this way, n-butanol is removed from the fermentor as it is produced, thereby allowing the microorganism to produce n-butanol at higher productivity.

WO 2011/160030 for example utilizes liquid-liquid extraction as ISPR in a method and system for efficiently producing a fermentative product alcohol such as n-butanol.

DE 102011080611 describes a method for separating volatile compounds from fermentation broths. Organophilic pervaporation membranes are mounted inside a fermentation reactor to withdraw volatile compounds from the reactor. A second stream is withdrawn from the reactor and passed over a filtration membrane to obtain a permeate comprising water and smaller molecules, while the retentate comprises biomass, undissolved particles and non-fermentative macromolecules and is partially recycled to the reactor.

Despite these efforts, the above methods still remain quite energy-intensive, in particular because they require performing pumps which provide for sufficient cross-flow streams on the membranes to avoid fouling and concentration and temperature gradients. Furthermore, substantial peripheral components are required around the reactor in order to obtain the above efficiency improvements.

SUMMARY

It is therefore an aim of the present description to provide methods and apparatuses which overcome the above drawbacks. In particular, it is an aim to provide methods and apparatuses which are more efficient in producing such compounds. It is furthermore an aim of the present description to provide methods and apparatuses which have a reduced complexity and/or allow for simplifying downstream processing.

According to a first aspect, there is therefore provided a method as set out in the appended claims. The method comprises adding a substrate to a medium, such as a reaction liquid, comprised in a reactor and reacting the substrate in the reactor to form a compound, such as an ester, an amide, or an organic solvent such as acetone and/or butanol. Advantageously during the reacting step, a first stream is separated or withdrawn from the medium through a first membrane, advantageously a semipermeable membrane. The first stream comprises first products. Advantageously, a catalyst is mixed with the medium in the reactor, and the first membrane is configured for retaining the catalyst. Advantageously simultaneously with separating the first stream, a second stream is separated or withdrawn from the medium through a second membrane, advantageously a semipermeable membrane. The second stream comprises second products distinct from the first products. Either the first products, or the second products may comprise the compound. The first stream and the second stream are withdrawn separately from the reactor.

According to an aspect, the first membrane and the second membrane, which are advantageously (at least partially) immersed in the medium, are moved relative to the reactor during the steps of separating the first stream and separating the second stream. Advantageously, the above separation steps are carried out in parallel, e.g. simultaneously. The first membrane is advantageously a filtration membrane, e.g. a microfiltration or ultrafiltration membrane. The second membrane is advantageously configured for liquid-gas or liquid-liquid extraction, e.g. a pervaporation membrane, or a contactor membrane respectively. Advantageously, the first and second membranes are mounted to respective support frames which are configured to turn on a common pivot axis or separate pivot axes arranged in a fixed position relative to the reactor.

According to a second aspect, there is provided an apparatus as set out in the appended claims. The apparatus may be configured to carry out a method according to the above aspects. The apparatus comprises a reactor, a first membrane unit and a second membrane unit. The first membrane unit is a filtration unit, advantageously comprising one or more filtration membranes. The second membrane unit advantageously comprising one or more membranes configured for liquid-gas or liquid-liquid extraction, respectively, such as a liquid-gas (pervaporation) or liquid-liquid (membrane contactor) extraction unit. The reactor comprises a reactor vessel, a substrate supply port, and either one or both of a first outlet port and a second outlet port. The first membrane has a first surface communicating with the reactor vessel and a second surface, opposite the first surface, communicating with the first outlet port. The second membrane has a third surface communicating with the reactor vessel and a fourth surface, opposite the third surface, communicating with the second outlet port. The first membrane is advantageously configured for transport of one or more first compounds from the first surface to the second surface, e.g. the first membrane is a semipermeable membrane. The second membrane is advantageously configured for transport of one or more second compounds from the third surface to the fourth surface, e.g. the second membrane is a semipermeable membrane. According to an aspect, the first membrane and the second membrane are arranged inside the reactor vessel. According to another aspect, either one or both of the first membrane and the second membrane is moveably arranged relative to the reactor vessel. Advantageously, the first surface and the third surface are accessible in parallel from the reactor vessel. Advantageously, the first membrane and the second membrane are mounted in the reactor vessel such that they are at least partially immersed in a reaction liquid when in use.

The apparatus can comprise first and second support frames to which the first membrane and the second membrane are respectively fixed. The first and second support frames can be pivotally arranged relative to the reactor vessel, e.g. they can turn on a common pivot axis or separate pivot axes arranged in fixed position relative to the reactor vessel.

By moving the membranes relative to the reactor, less pumping energy is required for sustaining a desired cross flow over the membrane surface. Furthermore, by appropriately maintaining the medium in motion relative to the membranes simplifies the requirements for substrate supply control, such as for temperature and concentration gradient control. Temperature gradients are minimized, and concentration gradients over a surface of the membranes can be minimized. A further advantage of the apparatuses and processes described herein is that they are inherently safer because no associated (external) loops with high cross flows are involved. There is no or less external piping which may be prone to leakage and/or which may expose maintenance operators to (potentially) toxic products. A further advantage is that they allow for integrating the membranes within the reactor vessel resulting in reactors with small footprints, taking much less space in comparison to prior art designs.

BRIEF DESCRIPTION OF THE DRAWINGS

Aspects of the present disclosure will now be described in more detail with reference to the appended drawings, wherein same reference numerals illustrate same features and wherein:

FIG. 2A represents a horizontal respectively vertical cross section of a reactor according to aspects described herein, wherein two membrane units are mounted on rotating supports within the reactor vessel;

FIG. 2B represents a cross section view along section line A-A;

DETAILED DESCRIPTION

Figure 1:
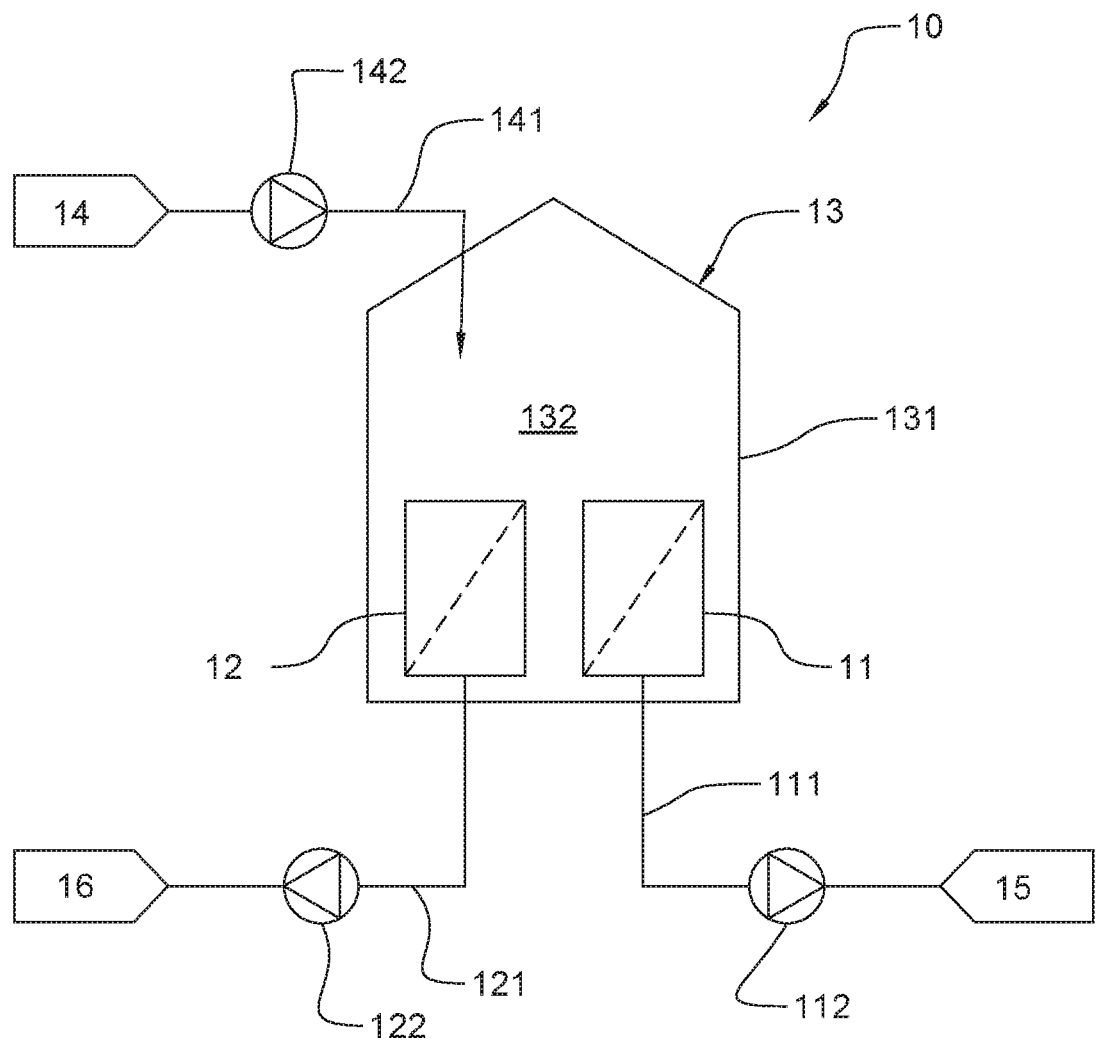
FIG. 1 represents schematically an apparatus integrating two separate membrane units in the reactor according to aspects described herein.

Referring to FIG. 1, an apparatus 10 according to aspects described herein, integrates two separate, distinct membrane units 11 and 12 within a reactor 13. Reactor 13 is advantageously a reactor for conversion of a substrate 14, in particular a biomass substrate, to a useful product such as an ester or amide, in the presence of a catalyst, advantageously a biocatalyst, such as microorganisms or enzymes. Reactor 13 comprises a reactor vessel 131 containing a reaction liquid 132 including (partially) converted and non-converted feedstock, and optionally the catalyst. Substrate 14 is advantageously continuously supplied to the reactor vessel 131 of reactor 13 through a supply duct 141 via a pump 142. The substrate 14 advantageously comprises substrate compounds for the catalyst for carrying out the conversion reactions.

The catalyst is advantageously housed in the reactor 13 (reactor vessel 131), and may or may not be immobilised therein. The catalyst is advantageously mobile in the reactor 13, e.g. it is mixed or suspended in the reaction liquid. Reaction products are advantageously continuously or intermittently (e.g., after depletion of a substrate) removed from the reactor 13 through membrane units 11 and 12. Each of the membrane units 11 and 12 is advantageously configured to recover or withdraw specific reaction products. Either one, or both the membrane units 11 and 12 advantageously allow for retaining the catalyst in the reactor 13.

A first membrane unit 11 may be configured to withdraw a first stream 15 from reactor 13. Membrane unit 11 advantageously comprises semipermeable membranes for producing the first stream 15 as a permeate stream from the reaction liquid 132 in the reactor 13. By way of example, membrane unit 11 is configured as a filtration unit, comprising filtration membranes. Membrane unit 11 is coupled to an outlet duct 111 at the permeate side. A pump 112 in communication with the outlet duct 111 may be configured for installing a desired pressure difference across the membranes of membrane unit 11.

The first stream (permeate) 15 advantageously comprises, or consists of a desired product to be recovered, such as an ester or an amide compound. The desired product may be formed through conversion processes occurring in the reactor 13, e.g. esterification and amidation reactions. Additional compounds present in reaction liquid 132 may permeate through the membrane unit. The desired product may be recovered from the first stream 15 through appropriate downstream processing, e.g. by distillation. Unconverted substrates may permeate through the membrane unit 11. These permeated substrates can be recycled to the reactor 13 after separation from the product to improve substrate utilization.

The membranes of membrane unit 11 are advantageously filtration membranes. Specific examples of suitable filtration membranes are microfiltration and ultrafiltration membranes. Another example of useful filtration membranes are nanofiltration membranes.

A second membrane unit 12 may be configured to withdraw a second stream 16 from reactor 13. The second membrane unit 12 is advantageously configured for withdrawing the second stream 16 through pervaporation (or liquid-gas extraction) or liquid-liquid extraction. To this end, the second membrane unit 12 may comprise one or more semipermeable membranes. In a first alternative, the second membrane unit 12 may be provided as a pervaporation unit, comprising semipermeable membranes which are advantageously suitable for use in pervaporation processes. Alternatively, the second membrane unit 12 may be provided as a membrane contactor unit, comprising contactor membranes suitable for liquid-liquid extraction.

In one embodiment, a pervaporation unit separates the second stream 16 from the medium in the reactor through permeation and evaporation of the second stream 16. In liquid-liquid extraction, a contactor membrane is used, over which a liquid phase is made to circulate at the permeate side. A difference in solubility or a concentration gradient provides the driving force to generate a mass transfer of selective compounds across the membranes, hence forming the second stream 16. The second membrane unit 12 is coupled to an outlet duct 121 at the permeate side of the unit. A pump 122, e.g. a vacuum pump in case of a pervaporation unit, may communicate with the outlet duct 121 side of the second membrane unit 12 to maintain a desired (partial vacuum) pressure level, or circulating flow (in case of liquid-liquid extraction).

The second stream 16 may comprise or consist of the compound, such as n-butanol in the exemplified (ABE) fermentation process or the second stream 16 may comprise or consist of a by-product of conversion reactions occurring in the reactor 13, such as water and/or alcohols in the exemplified enzymatic production of esters or amides. The by-product may be an inhibitory compound which is formed from the conversion reactions, such as water and/or an alcohol, e.g. methanol in the example below. An inhibitory compound refers to a compound which prevents further conversion of the substrate to the desired product to take place in reactor 13, in particular because of an equilibrium being reached between the reagents, e.g. the substrate, and the reaction products. By removing the inhibitory compound, a rate of formation of the desired products can be increased. Furthermore, by removing the inhibitory compound, the catalyst may be protected from inactivation.

According to an aspect, the membranes of the first membrane unit 11 and the membranes of the second membrane unit 12 are arranged inside the reactor 13. The membranes are advantageously at least partially and preferably fully immersed in the reaction liquid of the reactor. In particular, these membranes are arranged inside the vessel 131 of the reactor.

A pervaporation or membrane contactor unit integrated within the reactor vessel simplifies the requirements for temperature and concentration gradient control. Temperature gradients are minimized, and concentration gradients over a surface of the membranes can easily be minimized by appropriately maintaining the reaction liquid 132 in motion relative to the second membrane unit 12. A same reasoning may apply to a membrane filtration unit, such as the first membrane unit 11.

According to an aspect, and referring to FIGS. 2A-B, the membranes of units 11 and 12 are moveably arranged within the reactor 13. In particular, the membranes of units 11 and 12 are arranged to move relative to the reactor 13 (reactor vessel 131). Each of the first and second membrane units 11, 12 may comprise a support frame 113, 123 respectively which is pivotally arranged relative to reactor vessel 131. Support frames 113, 123 may be configured to turn on pivot axes 114, 124 fixed to the reactor vessel 131, such as through a rotating or oscillating motion.

Respective membranes 115, 125 of the first and second membrane units 11, 12 are mounted to the respective support frames 113, 123. The membranes are advantageously fixedly attached to the respective support frames. Each of the membranes 115, 125 comprise a first, outer surface in (direct) contact with, and advantageously immersed in the reaction liquid 132, and an opposite, second (inner) surface which communicates with the respective outlet duct 111, 121, e.g. through an appropriate manifold, which may be integrated in frame 113, 123. The membrane 115, 125 advantageously provides for transport of compounds from the outer surface to the inner surface, while other compounds may be retained or rejected at the outer surface. The membranes 115, 125 are advantageously hollow fibre membranes or tubular membranes, even though planar membranes, so called flat sheet membranes, and which may be arranged flat (e.g. to act like impellers) or may be spirally wound, can be used as well. The support frames 113, 123 and the disposition of the membranes 115, 125 thereon may have any desired configuration. Specific, non-limiting examples of such a configuration are support frames formed as radial brackets (as shown in FIG. 2A), concentric rings, brackets winding spirally about the pivot axis, etc.

When the support frames 113, 123 with the membranes 115, 125 are turned on axes 114, 124, the reaction liquid is advantageously mixed. The support frames and membranes therefore may be used in replacement of, or additional to impellers in the reactor. This minimizes concentration and temperature gradients in the vessel, minimizes concentration polarization effects on the surface of the membranes and/or reduces fouling of the membranes 115, 125. The motion of support frames 113, 123 may be continuous or intermittent.

Specific examples of this motion are a continuous rotation on axes 114, 124, and an oscillating motion, e.g. back and forth on axes 114, 124, advantageously over an angle ranging between 120° and 240°, e.g. 180°. An actuator, such as an electric motor, possibly arranged outside the reactor vessel 131, may be coupled to the axis 114 and/or 124 to provide the pivoting motion.

Figure 3:
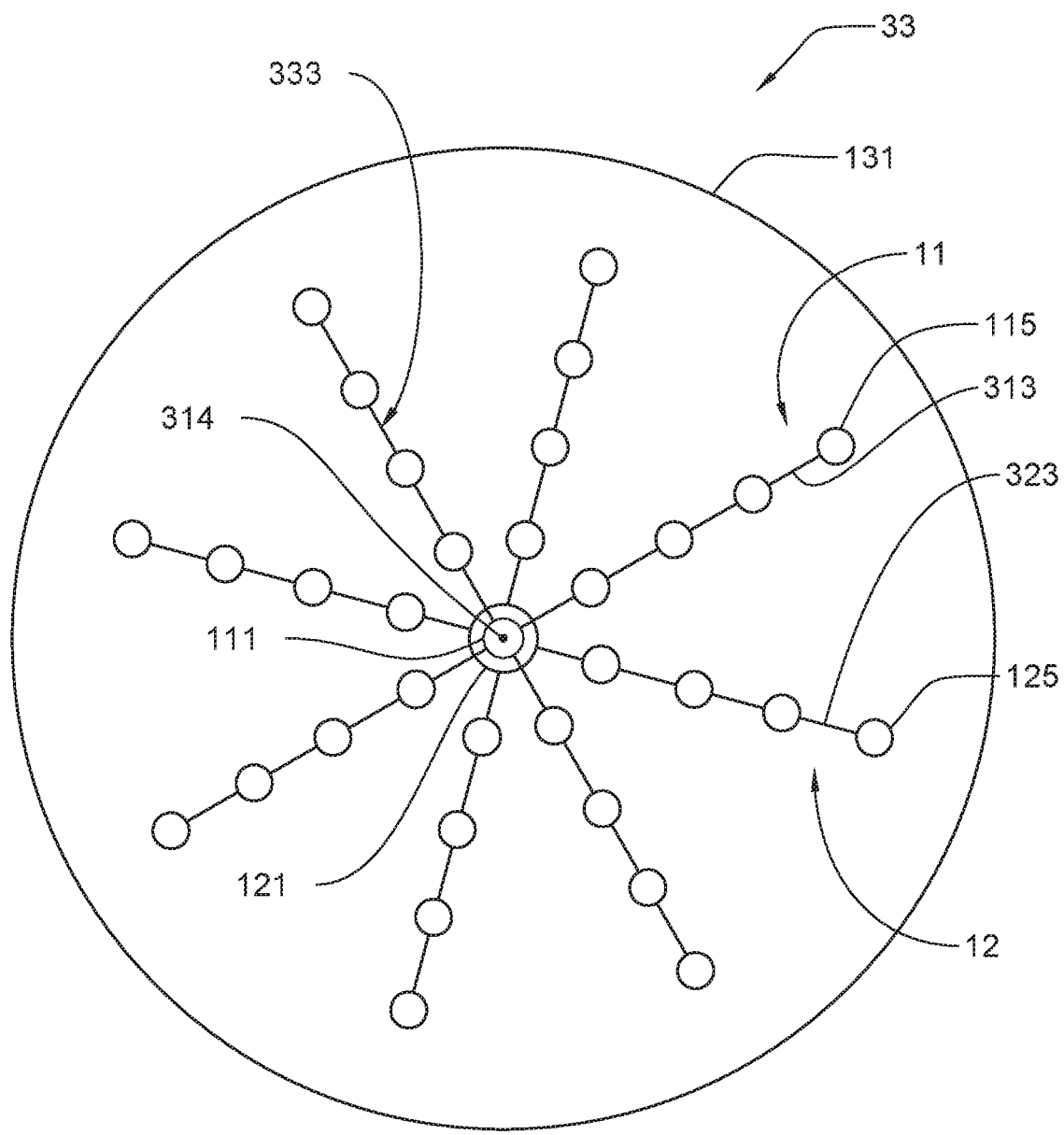
FIG. 3 represents a (horizontal) cross section of an alternative reactor compared to FIG. 2A, wherein the two membrane units are mounted on a single rotating support within the reactor vessel.

FIG. 3 shows an alternative configuration of a reactor 33. Reactor 33 differs from reactor 13 in that the membrane units 11, 12 are mounted on a common support frame 333, which is pivotally arranged on axis 314 fixed with respect to reactor vessel 131. Support frame 333 advantageously comprises first brackets 313 onto which the membranes 115 relating to the first membrane unit 11 are mounted, and second brackets 323 onto which the membranes 125 relating to the second membrane unit 12 are mounted. The first and second brackets may be disposed as desired on pivot axis 314. By way of example, the first and second brackets may be disposed alternatingly about axis 314. Each one bracket 313, 323 advantageously comprises a collector manifold for collecting the respective first and second streams 15, 16 from the membranes, and communicating with the corresponding outlet duct 111, 121.

As with reactor 13, the support frame 333 of reactor 33 may be configured to turn on axis 314 with any desired motion, e.g. (continuous) rotation or oscillation. The shape of the support frame is not particularly limited, and any suitable shape and/or disposition of the brackets 313, 323 may be used. Possible configurations for the support frame and which can be used in the reactors described herein, are described in US 2009/0034358 to Brod et al. and U.S. Pat. No. 8,328,167 to Kauling et al. It should be noted that in the above documents, the rotating membrane units are configured for gassing of liquids, whereas in the present description the rotating membrane units are configured for withdrawing two distinct streams from the reactor medium.

The support frames 113, 123 of the first and second membrane units 11, 12, or the support frame 333 placed inside the reactor vessel 131, are advantageously moved relative to the reactor, e.g. by imparting a pivoting motion on axis 114, 124 or 314 oscillating back and forth over a predetermined angle, e.g. 180° or smaller.

The membranes 115, 125 mounted on the respective support frame are in contact with the reactor medium. As the membranes move integrally with the support frame, a relative motion between the reactor medium and the membranes is sustained. In the examples of FIGS. 2A-B and 3, the (hollow fibre) membranes have longitudinal axes oriented parallel to the pivot axes 114, 124, 314, and therefore are oriented perpendicular to the plane of motion. These configurations may be effective in maintaining a sufficient level of cross flow of the reactor medium over the external surface of the membranes.

It will be convenient to note that filtration membranes are just one exemplary type of membranes that can be used in the apparatuses and processes described herein, e.g. in the first membrane unit 11. Other possible membranes may be configured to entrain a selective mass transfer across the membranes via mechanisms other than differential pressure and/or characteristic pore size, such as though not limited to: characteristic attraction of specific charge types (e.g. an ion exchange membrane), selective sorption, or solution or diffusion characteristics, e.g. membrane contactors.

Production of Esters or Amides

The reactor configurations described above in relation to FIGS. 1-3 are advantageously used for processes involving forming esters or amides.

According to one aspect, the above reactor configurations are used in a process of forming an ester, in particular a chiral ester. Different methods for forming esters exist, and all of them are in principle contemplated in the present description. One method of forming esters involves direct esterification. An alcohol and an organic acid, e.g. a carboxylic acid, are used as substrates and made to react to form the ester and water. Another method involves transesterification. An alcohol and an ester, e.g. methyl ester, are used as substrates and are made to react to form the ester and an alcohol, e.g. methanol. Other possible methods of forming esters involve alcoholysis of acyl chlorides or acid anhydrides.

Methods according to aspects described herein are particularly interesting for ester production where one and/or both substrates are volatile and/or forms azeotropes with methanol or water. In such cases, nitrogen stripping is rendered complicated due to downstream process complications. Examples of useful esters that may be produced in methods described herein are: isopropyl esters, methacrylate esters and acrylate esters.

According to another aspect, the above reactor configurations are used in a process of forming an amide, in particular a chiral amide, in particular an organic amide. Different methods for forming amides exist, and all of them are in principle contemplated in the present description. In one method of forming amides, an advantageously organic amine and an organic acid, e.g. a carboxylic acid, are used as substrates and made to react to form an (organic) amide and water. Other possible methods involve using acid anhydrides or acyl chlorides.

Methods according to aspects described herein are particularly interesting for production of amides where one of and/or both the substrates are volatile and/or form azeotropes with methanol/water. In such cases, nitrogen stripping is rendered complicated due to downstream process complications. Examples of useful processes include amide production processes where isopropyl amine or n-propyl amine is used as substrate, or where (meth)acrylic acid, or (meth) acrylate esters are used as substrates.

The substrates are supplied to reactor 13 or 33. Substrate pump 142 may be configured to supply substrates in controlled amounts to the reactor. Substrates may be pre-mixed prior to being supplied to the reactor, or they may be fed separately to the reactor. A catalyst may be provided in the reactor, either immobilized or freely suspended in the reactor. The catalyst is advantageously a biocatalyst, and processes described herein are advantageously biocatalytic processes. The (bio)catalyst advantageously comprises or consists of an enzyme, such as a lipase or an esterase. Examples of useful catalysts include lipases from *Candida antarctica*, from *Burkholderia* species, from *Fervidobacterium nodosum*, from *Starmerella bombicola*. A commercial name of an immobilised lipase is Novozym® 435 (Novozymes, Denmark) which is immobilised on acrylic resin. The enzyme, such as the lipase, may be freely suspended in the reactor or may be immobilized on a carrier. The (bio) catalyst may be a microorganism which may catalyze the reactions through an enzyme contained therein.

The substrates, e.g. supplied through stream 14, react in the reactor, possibly in the presence of the (bio)catalyst, to form the ester or the amide, and water or an alcohol, which build up in the reaction liquid 132. Reaction conditions in the reactor are advantageously mild, and temperature of the (reaction liquid in the) reactor may be maintained at between 30° C. and 70° C., advantageously between 40° C. and 65° C., advantageously between 50° C. and 60° C. Advantageously, no (organic) solvents are used in the reaction liquid 132 to form the ester or the amide.

In the first membrane unit 11 a suitable pressure difference across the membranes 115 (the transmembrane pressure) is advantageously applied, e.g. via pump 112. This will withdraw a first stream (permeate) from the reaction liquid which is collected in permeate channels (e.g., the internal lumens of membranes 115) of the membrane unit 11 and further evacuated via a collector manifold to the outlet duct 111. Through suitable selection of the type of membrane 115 (e.g., microfiltration, ultrafiltration, etc.), specific compounds may be selectively recovered from the reaction liquid, e.g. on the basis of molecule size. These compounds advantageously comprise the ester or the amide that is obtained through reaction in the reactor. Possibly, a portion of the substrate(s) may pass through the membranes 115. Membranes 115 may be selected to block passage of the (bio)catalyst, which will be retained in the reactor.

The permeate collected by the membranes 115 forms a first stream 15, which may be further processed via an appropriate downstream processing to separate the different compounds from which it is composed. The desired ester or amide can e.g. be recovered from stream 15 by distillation. Other compounds (e.g. the substrates) may be recovered, and may be recycled to the reactor 13, 33.

The membranes 125 of the second membrane unit 12 will withdraw a second stream 16 from the reaction liquid. The second stream 16 may comprise more than one compound originating from the reaction liquid. At least one of these compounds is advantageously different from the compounds collected in the first permeate by membranes 115 of the first membrane unit. In the instant embodiment the second stream advantageously comprises reaction (by-)products such as water or the alcohol, which are withdrawn from the reaction liquid 132 so as to shift the reaction to the right hand side and increase product titres. The second stream 16 may be condensed to a liquid phase and may be separated into its separate compounds by an appropriate downstream processing.

Pervaporation membranes 125 may be porous or nonporous membranes allowing a selective mass transfer driven by a partial vapor pressure gradient between substrate and permeate side. In nonporous membranes, a sorption-diffusion-desorption process is sustained through the membrane. Membranes for pervaporation are typically thin film composite membranes, comprising a separation layer defining the membrane characteristics provided on a porous support. Materials for the separation layer useful for pervaporation purposes may be made from a polymer material, a zeolite, a ceramic material or combinations thereof (e.g., polymer membranes with zeolite or ceramic filler particles). The membranes may be either hydrophilic, or organophilic (hydrophobic). Specific examples of useful hydrophilic membranes are made of polyvinyl alcohol, A-type (NaA) or Y-type (NaY) zeolites, or (hybrid) silica. Specific examples of useful hydrophobic membranes are made of polydimethylsiloxane (PDMS) or ZSM-5 (MFI) zeolite.

Hydrophilic pervaporation membranes are advantageously used for withdrawing water from the reaction liquid. For withdrawing the alcohol product from the reaction liquid, organophilic pervaporation membranes may be used. Alternatively, hydrophilic membranes may be used to withdraw the alcohol product.

Membranes used in membrane contactors may be porous or nonporous membranes. In non-porous membranes, a sorption-diffusion-desorption process is sustained through the membrane. Also here, membranes are typically thin film composite membranes. Materials for the separation layer useful for membrane contactor purposes may be made from a polymer material, a zeolite, a ceramic material or combinations thereof.

One advantage of the apparatuses and processes described herein is that they are inherently safer because no associated (external) loops with high cross flows are involved. There is no or less external piping which may be prone to leakage and/or which may expose maintenance operators to (potentially) toxic products. A further advantage is that it has a small footprint, taking much less space in comparison to prior art designs. Yet an additional advantage is that due to the integration of the membrane units 11 and 12 within the reactor, required pumping energy is greatly reduced.

It will be convenient to note that additional membrane units may be integrated in the reactor, similarly to the principles for the first and second membrane units 11, 12 described herein. By way of example, a third membrane unit may be provided in the reactor, either on a separate support frame, or integrated on the support frame of either or both the first and the second membrane units. The support frame of the membranes of the third unit may be pivotally arranged relative to the reactor, or alternatively may be fixed within the reactor. The third membrane unit may be configured for dosing liquid or gaseous compounds to the reaction liquid, through suitable porous or nonporous membranes. Additionally, a fourth, fifth and even further membrane units may be provided.

It will be convenient to note that, although the reactor 13 is described herein as formed of a single vessel (e.g., a single stage reactor), this is no requirement and apparatuses and methods described herein are applicable to multi-stage reactors. A multi-stage reactor typically comprises a plurality, e.g. two, three or even more reactor vessels arranged in series or in cascade. In such cases, the first membrane unit 11 and the second membrane unit 12 need not be arranged in a same reactor vessel, and may be arranged in different ones. Alternatively, it is possible to provide either one, or both the first membrane unit 11 and the second membrane unit 12 in more than one reactor vessel.

Production of Organic Solvents

Figure 4A:
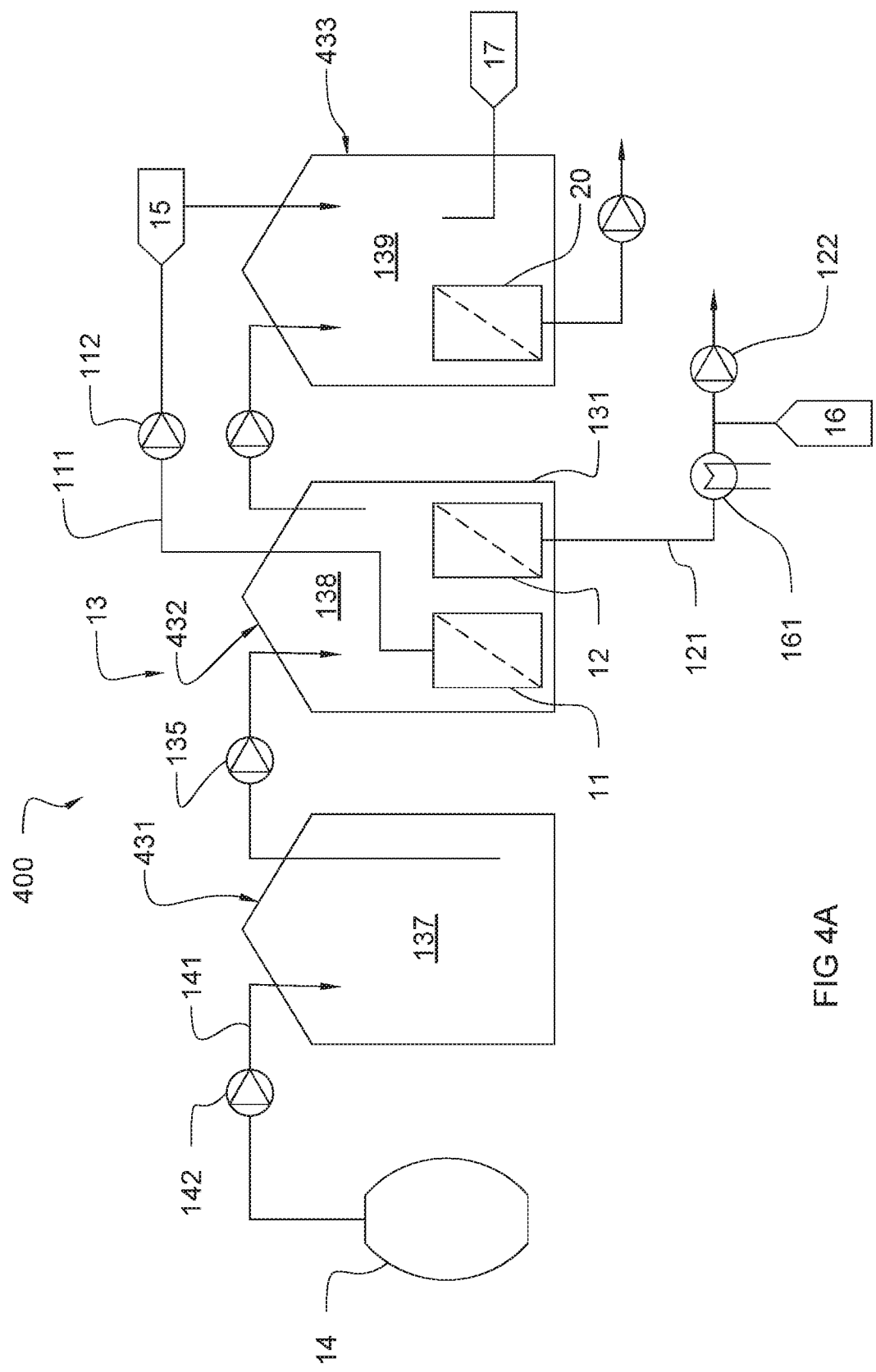
FIG. 4A represents schematically an apparatus integrating two separate membrane units in the reactor according to aspects described herein.

Referring to FIG. 4A, an apparatus 400 according to another aspect described herein integrates two separate, distinct membrane units 11 and 12 within a reactor 13. Reactor 13 is advantageously a reactor for conversion of a feedstock 14, in particular a biomass feedstock, to a useful product, in particular an organic solvent, or a mixture of a plurality of organic solvents. The conversion may be assisted by a suitable (bio)catalyst, such as a microorganism and/or an enzyme. Feed 14 is advantageously continuously supplied to the reactor 13 through a supply duct 141 via a feed pump 142.

The conversion reaction(s) in present aspects advantageously refer to fermentation reactions, including fermenting a feedstock in the presence of microorganisms, such as microorganisms of the *Clostridium* genus, in particular *Clostridium acetobutylicum*. The fermentation reaction(s) are advantageously all or in part carried out under anaerobic conditions.

Reactor 13 may be a single stage reactor, e.g. comprising a single vessel in which the feedstock 14 is converted; or a multi-stage reactor, comprising a plurality of reactor vessels arranged in series or in cascade, in which the conversion/fermentation reactions are carried out in a stepwise manner. By way of example, the reactor can be a two-stage reactor, or a three-stage reactor, as shown in FIG. 4A. The three-stage reactor comprises a first reactor 431 serially coupled to a second reactor 432, which in turn is serially coupled to a third reactor 433. The first reactor 431 comprises a first medium 137, which may comprise partially converted feedstock 14 and may also comprise residual feedstock that is not converted in the first reactor 431. Medium 137 is advantageously continuously withdrawn from the first reactor and supplied to the second reactor 432, e.g. via a pump 135. The second reactor 432 comprises a second medium 138, in which the medium 137 of the first reactor, which may contain residual feedstock 14, is further reacted. The second medium 138 may already comprise desired reaction products, such as a mixture of ABE solvents. The second medium 138 is advantageously continuously withdrawn from the second reactor and supplied to the third reactor 433, in which residual feedstock, such as residual carbohydrates, can further be converted in reactor medium 139. A third stream 17 may be withdrawn from the third reactor 433. It will be convenient to note that any one or all of the media 137, 138, 139 may be referred to as a fermentation broth.

Microorganisms may be present in any one or all of the first reactor 431, the second reactor 432, and the third reactor 433. By way of example, in the first reactor 431, an acidogenic fermentation may take place. In the second and third reactors 432 and 433, a solventogenic fermentation may take place. The third reactor may allow for maximizing solvent titers. The improved carbohydrate conversion will lower the substrate costs and the higher solvent titers will decrease the cost for further recovery of residual solvents. It will be convenient to note that more reactor stages may be added as desired, or any one of the first reactor stage and the third reactor stage may be omitted.

The feedstock 14 may comprise any suitable biomass. Feedstock 14 may originate from or comprise sugar cane, corn mash, or wheat. The feedstock 14 advantageously comprises carbohydrates, in particular hydrolysates, such as C5/C6 carbohydrates (such as starch, glucose, xylose), lignocellulosic hydrolysates, or hydrolysates from pulp and paper industry.

Advantageously, the fermentation reaction(s) in aspects of the present disclosure is (are) carried out at a temperature comprised between 30° C. and 45° C., advantageously between 30° C. and 40° C., advantageously between 32° C. and 38° C., advantageously between 35° C. and 37° C. This is obtained by maintaining the medium in reactor 13 (e.g. either one of the first reactor 431, second reactor 432, third reactor 433, or any combination thereof), at the temperature as indicated.

Advantageously, the pH of the medium in the reactor is maintained between 4.0 and 6.0, advantageously between 4.0 and 5.5, advantageously between 4.5 and 5.5, advantageously between 4.5 and 5.0.

Methods in aspects of the present description can be performed in a batch, fed-batch, or continuous manner, i.e. the feedstock 14 is provided (or introduced) in the reactor on a batch, fed-batch, or continuous basis.

The microorganisms are advantageously housed in the reactor, and may or may not be immobilised therein. Reaction products and possibly additional compounds, are advantageously continuously removed from the reactor through membrane units 11 and 12 as described hereinabove in relation to apparatus 10. Either one of, or both the membrane units 11 and 12 is advantageously configured to recover or withdraw specific compounds. The membrane units 11 and 12 advantageously allow for retaining the microorganisms in the reactor.

In this embodiment the first stream (permeate) 15 is advantageously withdrawn so as to increase cell concentration (of dry cell weights) in the reactor. This may advantageously result in an increase of feed (substrate) supply rates, solvent productivity and/or utilization of xylose. Additionally, the filtration membranes of the first membrane unit advantageously allow for retaining microorganisms and other possible catalysts in the reactor medium. This allows for increasing cell/microorganism concentration in the reactor, which may improve product conversion and may allow for reducing residence times of the feedstock in the reactor.

In this embodiment the second stream 16 may comprise or consist of a reaction product, such as the organic solvent, or the mixture of organic solvents. In the particular case of ABE fermentation, e.g. with *Clostridia* strains, the second stream may comprise or consist of one or more of, or consist of a mixture of: isopropanol, acetone, n-butanol and ethanol, and possibly water.

In the particular case that the second membrane unit 12 is a pervaporation unit, carbon dioxide ($CO_2$) generated by the fermentation reactions may advantageously be collected in the second stream. Due to the generally lower pressure at the filtrate side of the filtration membranes of the first membrane unit 11, $CO_2$ is locally oversaturated in the filtrate side and leads to $CO_2$ bubble formation in the filtrate side. This distorts liquid flows and leads to a difficult control of the residence time in continuous fermentations, which is required to ensure target productivities. The pervaporation membranes for solvent recovery operated in parallel with the filtration membranes do not only decrease the solvent concentration in the fermentation broths, they also remove $CO_2$. This results in an improved control of the residence time in the fermentation reactors by avoiding $CO_2$ bubble formation at the filtrate side of the filtration membranes.

Figure 4B:
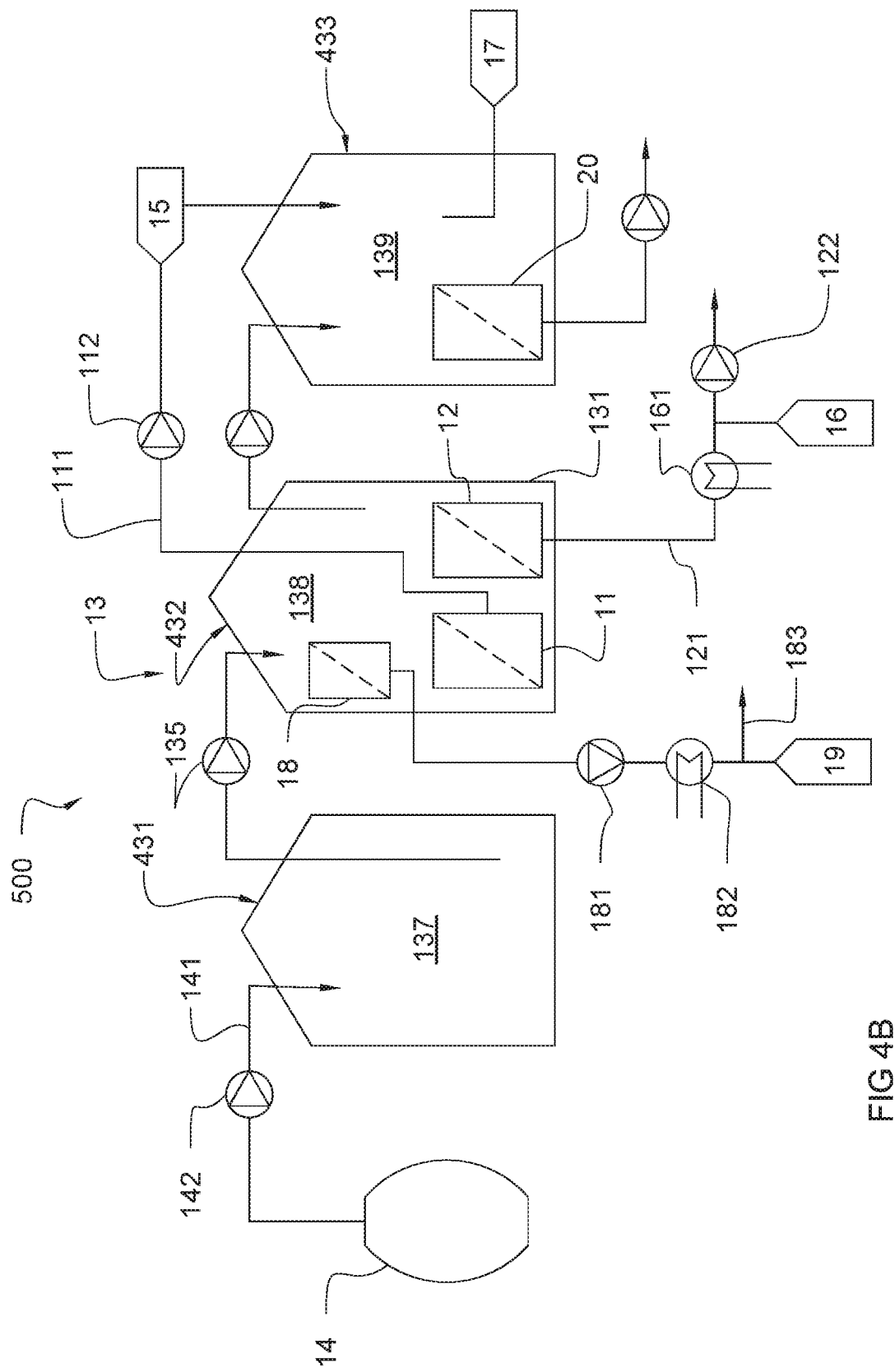
FIG. 4B represents schematically an alternative of the apparatus of FIG. 1A, in which a third membrane unit is further provided in the reactor.

Referring to FIG. 4B, an alternative apparatus 500 and related process scheme is provided. The apparatus and process scheme of FIG. 4B differs from the one of FIG. 4A in that a third membrane unit 18 is integrated in a similar way in the reactor 13, advantageously in the same reactor vessel as one or both of the other two membrane units 11 and 12. The third membrane unit 18 is configured to remove $CO_2$, $H_2$ and optionally other non-condensable gases. The third membrane unit 18 may be configured to operate as a membrane contactor, advantageously operating at a partial vacuum pressure at the permeate side. Suitable partial vacuum permeate pressures range between 75 mbar and 500 mbar, advantageously between 100 mbar and 400 mbar. At these relatively high permeate pressures (as compared to standard vacuum conditions), a negligible transfer of solvents occurs. Any solvents that may be transported through the membranes of the third membrane unit 18 may be condensed in a condenser 182 arranged downstream of a vacuum pump 181. The stream of solvents withdrawn through the third membrane unit 18 may be collected as a fourth stream 19 following removal of the non-condensable gases as a separate stream 183. Such a third membrane unit 18 can decrease overall vacuum costs. The presence of non-condensable gases greatly affects the operating costs of a vacuum pump, as shown in Van Hecke, W. and De Wever, H. in J. Membr. Sci. (2017), 540 (321-332). Hence, removal of the non-condensable gases in a separate loop at higher permeate pressures avoids excessive costs related to the vacuum (operating costs and number of vacuum pumps) in the second membrane unit 12.

According to an aspect, the membranes of the first membrane unit 11 and the membranes of the second membrane unit 12 are arranged inside the reactor 13, advantageously at least partially immersed in a medium 138 of the reactor. In particular, these membranes are arranged inside a vessel of the reactor. The reactor may be any one, or a plurality of the first reactor 431, the second reactor 432, and the third reactor 433. In the examples of FIGS. 4A-B, the membranes of the first and second membrane units are arranged in the vessel 131 of the second reactor 432, advantageously at least partially and advantageously fully immersed in the second reactor medium 138. In an alternative configuration, the membranes of one or both the first and second membrane units may be arranged in the vessel of the first reactor 431, and advantageously be immersed in the first reactor medium 137. By way of example, the membranes of the first membrane unit 11 may be arranged in the first reactor 431, while the first membrane unit is arranged in the second reactor 432. Yet alternatively, an additional membrane unit operating similarly to the first membrane unit 11 may be arranged in the first reactor 431

A pervaporation or liquid-liquid extraction unit integrated within the reactor vessel simplifies the requirements for temperature and concentration gradient control. Temperature gradients are minimized, and concentration gradients over a surface of the membranes can easily be minimized by appropriately maintaining the reactor medium 432 in motion relative to the second membrane unit 12. A same reasoning applies to a membrane filtration unit, such as the first membrane unit 11.

A fifth stream can be withdrawn from the medium as a bleed. The fifth stream may be smaller in comparison to the first stream and/or the second stream. The fifth stream advantageously allows for keeping a cell concentration constant in the reactor and hence, enables to operate the reactor in steady-state conditions. It will be convenient to note that the fifth stream need not, and typically will not be withdrawn through a membrane, since the purpose here is to remove part of the larger sized compounds (e.g., cells) from the reactor medium.

According to an aspect, the membranes of units 11 and 12 are arranged to move relative to the reactor 13 as already indicated above in relation to FIGS. 2A-B and FIG. 3. In particular, the membrane units 11 and 12 may be arranged in vessel 131 of the second reactor 432 and be arranged to move relative to the vessel.

It will be convenient to note that the first and second membrane units may each be disposed in any one of the available reactors 431, 432, 433 containing a reactor medium. By way of example, the support frame 113 and membranes 115 of the first membrane unit 11 may be arranged in the third reactor 433, while the support frame 123 and membranes 125 may be arranged in the second reactor 432.

In the first membrane unit 11, a suitable pressure difference across the membranes 115 (the transmembrane pressure) is advantageously applied, e.g. via pump 112. This will withdraw a first stream 15 from the reactor medium which is collected in permeate channels (e.g., the internal lumens of membranes 115) of the membrane unit 11 and further evacuated via a collector manifold to the outlet duct 111. Through suitable selection of the type of membrane 115 (e.g., microfiltration, ultrafiltration, etc.), specific compounds may be selectively recovered from the reactor medium, e.g. on the basis of molecule size. Membranes 115 may be selected to block passage of the microorganisms present in the reactor, which will be retained in the reactor. As a result, cell concentration in the reactor(s) is increased, which will increase consumption of feedstock and therefore increase production rate of the organic solvent(s). By way of example, even though Clostridial strains are known to consume C5 carbohydrates, consumption rates are observed to be low in comparison to C6 consumption rates. This hampers solvent productivities and leads to bulky fermentors. A filtration membrane unit allows cell retention and by consequence will lead to improved xylose conversion.

As shown in FIG. 4A and FIG. 4B, the first stream 15 may be introduced in another reactor stage, e.g. a downstream stage, such as the third reactor 433, or may be further processed to separate the individual compounds by an appropriate downstream processing, e.g. by distillation.

The pervaporation or contactor membranes 125 of the second membrane unit 12, when applying a suitable partial vacuum or reduced pressure at the internal membrane surface (permeate side), e.g. via pump 122, will withdraw a second permeate from the reactor medium which is collected in permeate channels (e.g., the internal lumens of membranes 125) of the membrane unit 12 and further evacuated via a collector manifold to the outlet duct 121 as the second stream 16. In case the second membrane unit 12 is arranged as a pervaporation unit, the second stream is typically collected at the internal face of membranes 125 as a vapor. The second stream 16 may comprise more than one compound. The second stream advantageously comprises volatile organic compounds, such as the organic solvent(s), and may comprise water. Withdrawing the organic solvent(s) from the reactor medium alleviates product toxicity and improves the water balance by increasing the carbohydrate utilization. The second stream 16 may be condensed to a liquid phase, e.g. through condenser 161, and may be separated into its separate compounds by an appropriate downstream processing.

It will be convenient to note that additional membrane units may be integrated in the reactor, similarly to the principles for the first and second membrane units 11, 12 described herein. Referring to FIGS. 4A and 4B, a fifth membrane unit 20 may be provided in the downstream reactor stage 433. The fifth membrane unit may be similar as the first membrane unit 11, e.g. arranged as a filtration unit comprising microfiltration or ultrafiltration membranes, or alternatively may be similar to the second membrane unit 12.

Furthermore, the third membrane unit 18 may be provided in the reactor, either on a separate support frame, or integrated on the support frame of either or both the first and the second membrane units. The support frame of the membranes of the third unit may be pivotally arranged relative to the reactor, or alternatively may be fixed within the reactor. Yet further membrane units may be provided, e.g. configured for dosing liquid or gaseous compounds to the reactor medium, through suitable porous or nonporous membranes.

Figure 5:
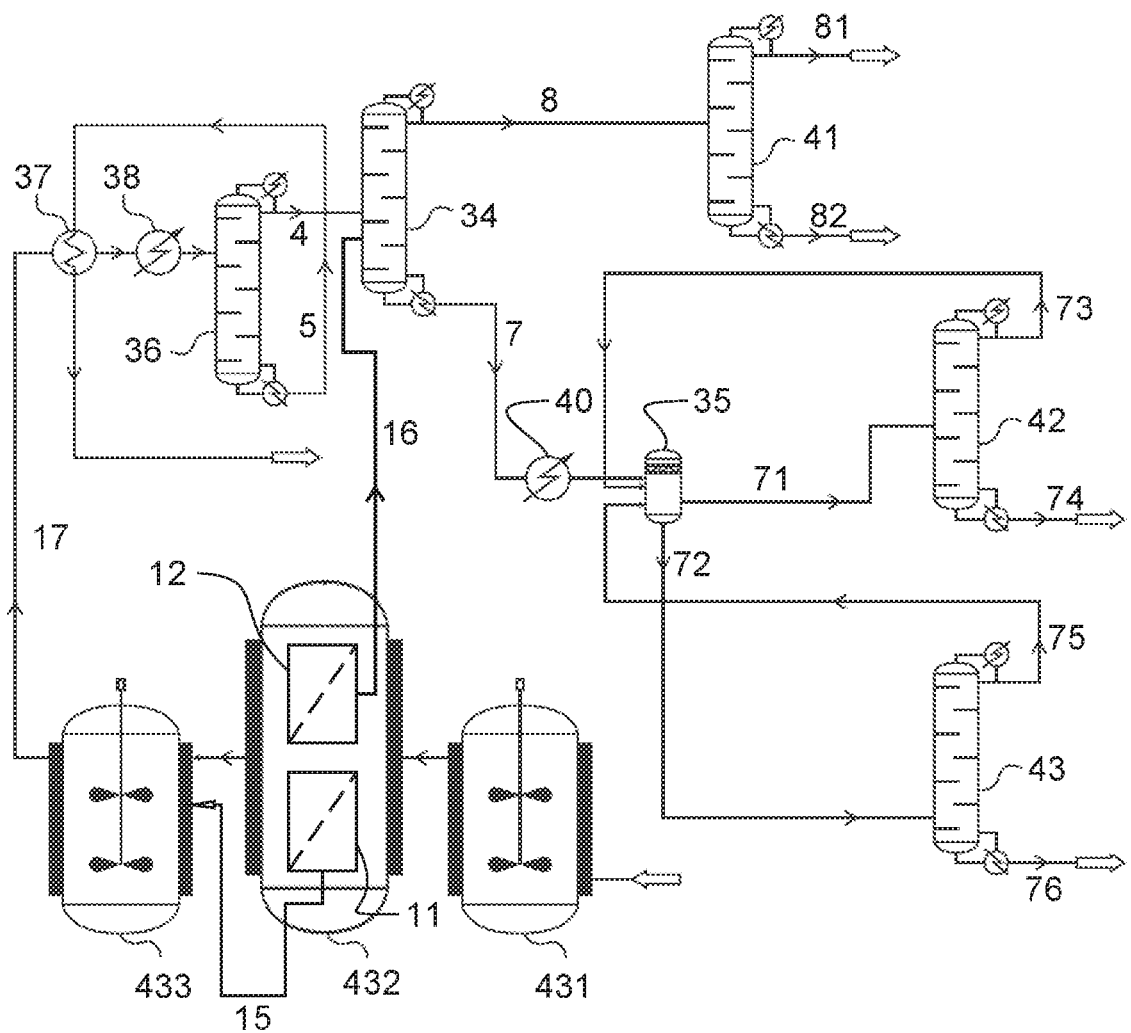
FIG. 5 represents a downstream process block diagram for the separation and purification of the streams recovered from the fermentation reactors of the apparatus of FIGS. 4A and 4B.

The reactor configurations described above in relation to FIGS. 4A-B are advantageously used for processes involving forming one or a mixture of organic solvents, as described herein, such as ABE. Conventional downstream processing may be applied to the second stream 16 and/or the third stream 17 to obtain the organic solvent at desired purity grades. One specific example of a possible downstream process for the second stream 16 and the third stream 17 will now be described in relation to FIG. 5, in particular for the case in which the second stream 16 originates from a membrane unit 12 being a pervaporation unit. The second stream 16 is supplied as feed to a first distillation column 34, possibly as a condensate following passing through a condenser 161 (see FIG. 4A-B). The second stream 16 is distilled in column 34 to produce an overhead stream 8, enriched in a first range of solvents, and a bottoms stream 7 which may be liquid, depleted in the first range of solvents. Distillation column 34 is advantageously a multistage distillation column, such as comprising a number of theoretical stages ranging between 6 and 35.

The third stream 17, or at least a portion thereof may also be fed to the first distillation column 34. To this end, third stream 17 can first be sent to a stripper, e.g. a steam stripper 36. In the context of the present description, a steam stripper refers to a beer stripper or steam distillation apparatus, known by those skilled in the art. The third stream 17 may be centrifuged for cell/particle removal prior to sending the (cell/particle-free) effluent to the stripper. In addition, or alternatively, third stream 17 may be heated, e.g. by passing through heat exchangers 37, 38, prior to being fed to the stripper. By way of example, heat exchanger 37 may be configured to heat stream 17 to a temperature comprised between 75° C. to 85° C., after which the stream 17 may be further heated by heat exchanger 38, e.g. to a temperature comprised between 90° C. to 95° C., and afterwards sent to the steam stripper 36. Steam stripper 36 produces a top (overhead) stream 4 which is fed to the first distillation column 34, where it is distilled in conjunction with the second stream 16 to produce bottoms stream 7 and overhead stream 8.

Bottoms stream 7, exiting the first distillation column 34 may comprise two phases, a solvent rich phase and an aqueous phase. In one specific example, the solvent rich phase comprises n-butanol and the aqueous phase comprises water. These two phases are subsequently separated in a suitable separator. By way of example, bottoms stream 7 is fed to a decanter 35, where stream 7 is separated in the solvent rich phase 71, and the aqueous phase 72. In ABE fermentative processes, the solvent rich phase 71 advantageously is mainly formed of n-butanol, e.g. at least 51% by volume. The aqueous phase 72 may comprise a lesser amount of n-butanol, e.g. less than 15% by volume, such as between 3% to 15% by volume n-butanol.

A heat exchanger 40 may be arranged between the first distillation column 34 and the decanter 35 to adjust a temperature of the bottoms stream 7 to a temperature suitable for decantation. A suitable temperature for decantation depends on the products, advantageously solvents, that need to be separated and will be apparent for those skilled in the art. By way of example, the temperature of stream 7 upon feeding to decanter 35 ranges between 35° C. and 45° C.

The solvent rich phase 71 is advantageously further purified, e.g. by distillation. To this end, phase 71 may be fed to a second distillation column 42, communicating with a first outlet of the decanter 35. Second distillation column 42 generates a bottoms stream 74 forming a first solvent, advantageously a substantially pure first solvent. In ABE fermentations, stream 74 advantageously comprises, or consists of (substantially pure) n-butanol. Advantageously, stream 74 consists of n-butanol having a purity comprised between 99.0% (w/w) and 99.9% (w/w), advantageously between 99.5% (w/w) and 99.9% (w/w), advantageously between 99.7% (w/w) and 99.9% (w/w), advantageously a purity of 99.8% (w/w).

The produced (substantially pure) n-butanol in aspects of the disclosure can be used as an intermediate in chemical industry. For example, the produced n-butanol can be used as a solvent, as a feedstock chemical in the plastics industry, as an ingredient in formulated products such as cosmetics, as a food grade extractant in the food and flavour industry, as a fuel, or as a fuel additive. The overhead stream 73 exiting second distillation column 42 can be recycled back to the decanter 35 for decantation.

The aqueous phase 72 exiting the decanter 35 as a bottoms stream is advantageously further purified, e.g. by distillation. To this end, phase 72 can be sent to a third distillation column 43, communicating with a second outlet of the decanter 35. The third distillation column 43 generates a bottoms stream 76 forming a substantially pure aqueous phase, depleted from organic solvent. Advantageously, stream 76 comprises only trace amounts of (organic) solvents, advantageously stream 76 comprises mainly water depleted from n-butanol. The third distillation column 43 generates an overhead stream 76 which can be recycled back to the decanter 35.

In an alternative embodiment, the aqueous phase 72 formed by decantation in the decanter 35 as a bottoms stream, can be sent to an extraction unit (not shown). In such an extraction unit, n-butanol is extracted out of water using a (bio)diesel or another fuel as extractant. This results in the production of a n-butanol enriched (bio)fuel, which can be further used as such.

Overhead stream 8 of the first distillation column 34 may comprise amounts of organic solvents. In ABE fermentation, for example, stream 8 may comprise a mixture of mainly acetone and ethanol. The obtained mixture comprising acetone and ethanol can directly be used in further chemical reactions. Alternatively, overhead stream 8 may be further purified/separated, e.g. by distillation to obtain a stream of (substantially pure) acetone and a separate stream of an azeotropic mixture of ethanol. To this end, overhead stream 8 can be sent to a fourth distillation column 41, communicating with a second outlet of the first distillation column 34. The fourth distillation column 41 generates an overhead stream 81 comprising, or consisting of a (substantially pure) second solvent and a bottoms stream 82 comprising a third solvent (and being depleted in the second solvent). In ABE fermentation, stream 81 advantageously comprises or substantially consists of acetone. The obtained acetone in stream 81 may have a purity comprised between 98.0% (w/w) and 99.9% (w/w), advantageously between 98.5% (w/w) and 99.5% (w/w), advantageously between 99.0% (w/w) and 99.5% (w/w). Stream 82 may be rich in ethanol. By way of example, stream 82 may be an azeotropic mixture (or azeotropic solution) comprising between 85% and 90% by volume ethanol and between 10% and 15% by volume water, advantageously between 86% and 88% by volume ethanol and between 12% and 14% by volume water, advantageously 87% by volume ethanol and 13% by volume water.

The invention claimed is:

1. A method of obtaining a compound, the method comprising:
   adding a substrate to a medium comprised in a reactor,
   reacting the substrate in the reactor to form the compound,
   separating a first stream from the medium through a first membrane by filtration, the first stream comprising first products,
   separating a second stream from the medium through a second membrane by liquid-gas or liquid-liquid extraction, the second stream comprising second products distinct from the first products, and
   withdrawing the first stream and the second stream separately from the reactor,
   wherein the first membrane and the second membrane are at least partially immersed in the medium and turn on one or more pivot axes relative to the reactor while separating the first stream and separating the second stream, wherein the one or more pivot axes are arranged in a fixed position relative to the reactor; and wherein either the first or the second products include the compound.

2. The method of claim 1, wherein the steps of separating the first stream and of separating the second stream are performed in parallel.

3. The method of claim 1, wherein the first membrane is a microfiltration, ultrafiltration or nanofiltration membrane.

4. The method of claim 1, wherein the second stream is separated through the second membrane via pervaporation or liquid-liquid extraction.

5. The method of claim 1, wherein the compound is an ester or an amide, wherein the first products comprise the compound, and wherein the second products comprise water or an alcohol.

6. The method of claim 5, wherein the reactor comprises a catalyst, the catalyst being retained by the first membrane.

7. The method of claim 6, wherein the catalyst comprises an enzyme.

8. The method of claim 1, wherein the compound is an organic solvent, and wherein the second products comprise the organic solvent.

9. The method of claim 8, wherein the organic solvent is butanol or acetone.

10. The method of claim 8, wherein the second stream is separated through the second membrane by pervaporation, the second stream comprising a gaseous compound, in particular carbon dioxide.

11. The method of claim 1, wherein the compound is obtained through a fermentation process.

12. The method of claim 1, wherein the first membrane and the second membrane are mounted on respective support frames arranged in the reactor, wherein the support frames turn on the one or more pivot axes relative to the reactor.

13. The method of claim 1, wherein the first membrane and the second membrane are rotating or oscillating on the one or more pivot axes relative to the reactor while of separating the first stream and separating the second stream.

14. The method of claim 1, comprising applying a pressure difference across the first membrane, thereby separating the first stream from the medium.

15. The method of claim 1, wherein the second stream is separated from the medium by pervaporation, wherein the second membrane is organophilic.

16. The method of claim 1,
wherein the reactor comprises a reactor vessel, a substrate supply, a first outlet, and a second outlet;
wherein the first membrane has a first surface communicating with the reactor vessel and a second surface, opposite the first surface, communicating with the first outlet, and
wherein a liquid-liquid or liquid-gas extraction unit comprises the second membrane having a third surface communicating with the reactor vessel and a fourth surface, opposite the third surface, communicating with the second outlet.

17. The method of claim 16, further comprising applying a first pressure difference between the first surface and the second surface of the first membrane, the first pressure difference generating a permeate flow from the first surface to the second surface.

18. The method of claim 16, further comprising applying a second pressure difference between the third surface and the fourth surface of the second membrane, the second pressure difference recovering a liquid compound in the reactor vessel through a corresponding vapor at the fourth surface.

19. The method of claim 12,
wherein a pair of pivot axes are fixedly coupled to the reactor, and each of the support frames turn on a respective one of the pivot axes; and
wherein a common pivot axis is fixedly coupled to the reactor, and the support frames turn on the common pivot axis.

* * * * *